| United States Patent [19] | [11] Patent Number: 4,786,504 |
| Forse et al. | [45] Date of Patent: Nov. 22, 1988 |

[54] COLORED INTAGLIATED ARTICLES

[75] Inventors: Sidney F. Forse, Macclesfield; Raymond C. Rowe, Congleton, both of United Kingdom

[73] Assignee: Imperial Chemical Industries, plc, London, England

[21] Appl. No.: 876,408

[22] Filed: Jun. 20, 1986

Related U.S. Application Data

[60] Division of Ser. No. 780,725, Sep. 27, 1985, Pat. No. 4,661,367, which is a continuation of Ser. No. 499,141, May 27, 1983, abandoned.

[30] Foreign Application Priority Data

Jun. 10, 1982 [GB] United Kingdom ................. 8216816

[51] Int. Cl.⁴ ........................... A61K 9/44; B44F 1/08
[52] U.S. Cl. ................................................. 424/467
[58] Field of Search ............................ 424/467; 427/3

[56] References Cited

PUBLICATIONS

E.P. 0060023, I.C.I., 9/82.

Primary Examiner—Sam Silverberg
Attorney, Agent, or Firm—Cushman, Darby & Cushman

[57] ABSTRACT

Colored intagliated articles, for example colored intagliated pharmaceutical tablets, on which the intagliations are highlighted. The articles are colored intagliated articles bearing a layer consisting essentially of a defined optically anisotropic substance, for example magnesium carbonate. Process for manufacturing said articles.

9 Claims, No Drawings

COLORED INTAGLIATED ARTICLES

This is a division of application Ser. No. 780,725, now U.S. Pat. No. 4,661,367, filed Sept. 27, 1985, which in turn is a continuation of application Ser. No. 499,141, filed May 27, 1983, now abandoned.

This invention relates to coloured intagliated articles on which the intagliations are highlighted.

In order that the invention may be the more easily comprehended, two expressions used in this specification will now be defined:

"intagliated article"—The word "intagliated" is related to the word "intaglio", which essentially means a figure or mark cut into any solid material. In one dictionary the word "intagliated" is defined as "incised" or "engraved". In the present specification the expression "intagliated article" means a solid article which has at least one figure, mark or notation, or any combination thereof, formed in the surface of the article by a compression punching, incision or engraving procedure, or by any other procedure which produces a like effect.

"optically anisotropic substance"—An anisotropic substance is one which shows differences of property or effect in different directions. As it is used in this specification, the expression "optically anisotropic substance" means any substance which exhibits different refractive indices in different directions and which has a minimum refractive index not greater than 2.00.

Various methods are used in the pharmaceutical industry for putting product names, active ingredient information, company identifying marks, and/or like information, on the surface of unit dosage forms such as tablets. For example, one known method involves applying printed information on to coated unit dosage forms, for example film coated tablets. Another method involves the use of intagliated unit dosage forms where the information is presented on the surface of the dosage forms in the form of intagliations. In the said method involving printed information the information can be applied in the form of one or more colours. However, printing is a relatively difficult, slow and costly procedure, and it involves the use of specialised machinery. By contrast, the process of this invention involves the use of coating apparatus (different versions of which are widely used in industry), and it is a cheap and rapid process. In the said known method involving intagliations, it has not been possible heretofore to produce intagliated unit dosage forms in which the intagliations are in a different colour from the remainder of the dosage form. The present invention remedies that deficiency.

We have found that if coloured (i.e. non-white) intagliated tablets (which may or may not already bear a film coat) are coated in a side-vented perforated coating drum with a suspension of a white optically anisotropic substance, the colour of the non-intagliated part of the tablets is very little changed from the original colour, but the intagliations appear essentially white, and therefore they are highlighted. That is, the intagliations show up in a distinctive and attractive way against a coloured background, and the intagliated information is much easier to read.

It is known to include an optically anisotropic substance such as calcium carbonate, magnesium carbonate, sucrose or lactose in film coating compositions but it is not known, nor is it obvious, to apply a suspension of an optically anisotropic substance to coloured intagliated articles in order to highlight the intagliations.

The present invention is capable of wide application, and it is to be understood tht it is not solely restricted to the pharmaceutical field. Thus, for example, it can be applied in the veterinary field, for example in the preparation of boluses (i.e. veterinary tablets), or in the confectionery field, for example in the preparation of sugar confectionery (i.e., sweets or candy) having approximately the same dimensions as pharmaceutical tablets or boluses, and in other fields where it is desirable to have intagliated articles in which the intagliations are highlighted.

It is to be understood that in this specification a coloured article means a non-white article.

According to the invention there is provided a coloured solid article bearing at least one highlighted intagliation, which comprises a coloured intagliated article bearing a layer consisting essentially of at least one optically anisotropic substance having a minimum refractive index not greater than 2.00.

It is to be understood that the said layer contains no film coating agent.

Prior to the application of the optically anisotropic substance the coloured intagliated articles may be uncoated, for example they may be uncoated medicinal tablets or boluses. Alternatively, they may bear at least one film coat, for example they may be film coated medicinal tablets or film coated pieces of sugar confectionery. The said film coat may comprise any film coating agent or agents known in the art, for example a cellulose ether, for example methylcellulose, ethylcellulose, hydroxyethylcellulose, hydroxypropylcellulose, hydroxypropyl methylcellulose or sodium carboxymethylcellulose, or a mixture thereof, or cellulose acetate phthalate, hydroxypropyl methylcellulose phthalate, polyvinyl acetate, polyvinyl acetate phthalate, cellulose acetate, shellac or an acrylic resin, or a mixture thereof. The film coat may contain one or more adjuvants which are conventional in the film coating art, for example plasticisers, surface active agents and/or waxes. The film coat is applied in conventional manner using conventional apparatus and using either an organic solvent-based coating process, for example a process involving a mixture of methylene dichloride and methanol, or an aqueous coating process.

The colour, which characterises the intagliated article prior to the application of the optically anisotropic substance, may be present throughout the article, or it may be applied to the surface of the article. Thus, a coloured substance, for example a coloured medicinal or veterinary agent in the case of medicinal or veterinary intagliated articles, or a colouring agent, may be present throughout the article. Alternatively, a coluring agent may be applied as such, or in the form of a coloured film coat, to the surface of the article. Any conventional colouring agent which is approved for the purpose in question, for example pharmaceutical purposes, may be used, for example iron oxide (red, yellow or black), carmine, natural dyes, for example turmeric or beta-carotene, water-soluble dyes, for example tartrazine, or aluminum lakes of water-soluble dyes, or any mixture thereof, optionally in admixture with at least one opaque white pigment, for example titanium dioxide.

It is to be understood that the general description hereinafter concerning the optically anisotropic substances, film coating agents and colouring agents which can be used according to this invention is phrased in the singular for ease of reading and comprehension, but it applies also to mixtures of two or more of said optically anisotropic substances, film coating agents and/or colouring agents.

The optically anisotropic substance is used according to this invention in the form of a powder. As suitable optically anisotropic substances there may be mentioned, for example, white optically anisotropic substances, for example, known transparent white pigments (also known as "extender" or "inert" white pigments), for example aluminium hydroxide, china clay (kaolin), talc, calcium carbonate or barium carbonate. Other suitable optically anisotropic substances are magnesium carbonate (light or heavy form), cane sugar (sucrose), lactose or tartaric acid. Alternatively, in the case of a medicinal or veterinary unit dosage form the medicinal or veterinary agent present therein may also be used as the optically anisotropic substance. That is, the medicinal or veterinary agent may be used in a dual role: as both the active agent in the unit dosage form and as the optically anisotropic substance.

As aforesaid, the optically anisotropic substance has a minimum refractive index not greater than 2.00. It is an advantage to use an optically anisotropic substance which has a maximum refractive index which is as different as possible from its minimum refractive index, as this affords the best visual results. Details on typical optically anisotropic substances which can be used according to the present invention are as follows:

| Optically anisotropic substance | Refractive indices | |
|---|---|---|
| | Minimum | Maximum |
| Aluminium hydroxide | 1.50 | 1.56 |
| Kaolin | 1.56 | 1.57 |
| Talc | 1.54 | 1.59 |
| Calcium carbonate | 1.51 | 1.65 |
| Calcium sulphate | 1.57 | 1.61 |
| Barium carbonate | 1.53 | 1.68 |
| Magnesium carbonate | 1.51 | 1.70 |
| Cane sugar | 1.54 | 1.57 |
| α-Lactose | 1.52 | 1.57 |
| Tartaric acid | 1.50 | 1.61 |

The amount of optically anisotropic substance that is applied depends upon the degree of colour contrast required, the refractive indices of the substance, and its particle size.

According to a preferred further feature of the invention, the articles of the invention may optionally carry, on top of the layer consisting essentially of at least one optically anisotropic substance, at least one film coat. The latter (hereinafter "outer") film coat(s) comprise(s) one or more conventional film coating agents and optionally at least one conventional film coating adjuvant, as described hereinbefore, and it is or they are applied in conventional manner. The outer film coat(s) may in additional comprise at least one colouring agent so as to provide at least one coloured outer film coat. Where more than one such coat is present, each such coat may contain the same or different colouring agent(s). The net effect of this embodiment of the invention is that the colours in question [i.e. the colour of the main body of the article and the colour of the intagliations, on the one hand, and the colour(s) of the outer film coat(s), on the other] interact in a subtractive manner [see Encyclopaedia Britannica, Micropaedia, Volume III, 1974, 22]. Numerous colour combinations are thus possible, the intagliations normally being seen as a pale version of the colour of the outer coat(s). If the colour of the main body of the article and heat of the outer film coat(s) are so-called complementary colours (see above references), the main body of the article is seen as black and the intagliations are seen as a pastel colour [i.e. a pale version of the colour of the outer coat(s)].

According to a further feature of the invention there is provided a process for the manufacture of coloured solid articles bearing at least one highlighted intagliation, which comprises applying to coloured intagliated articles a suspension comprising at least one optically anisotropic substance, having a minimum refractive index not greater than 2.00, in a suitable liquid in which the optically anisotropic substance is insoluble or of relatively poor solubility, which process is carried out in a conventional film coating apparatus in such a way that a rubbing action takes place between the articles being coated.

It is to be understood that the said suspension contains no film coating agent.

The coloured intagliated articles used as starting material may themselves be uncoated or film coated, and they are produced in conventional manner. For example, coloured intagliated medicinal or veterinary unit dosage forms are produced in conventional manner using appropriate active agents and conventional excipients.

The liquid used in the process of the invention depends upon (1) the optically anisotropic substance used, and (2) whether the said coloured intagliated articles are uncoated or film coated, and, if film coated, upon the water-solubility of the film coating agent. As regards (1), the liquid should be one in which the optically anisotropic substance is insoluble or of relatively poor solubility. As regards (2), if the articles are uncoated, or if they are film coated with a relatively water-soluble film coating agent, for example hydroxypropyl methylcellulose, a suitable liquid is, for example:

(a) water
(b) a mixture of water and a (1–4C)alkanol, for example ethanol;
(c) a mixture of a polyhalogenated (1–4C)alkane, for example methylene dichloride, and a (1–4C)alkanol, for example methanol; or
(d) a mixture of liquid (c) and a dialkyl ketone of not more than 6 carbon atoms, for example acetone.

The said liquid (a) may optionally contain at least one surface active agent, for example polyoxyethylene sorbitan monooleate ['Tween' (Trade Mark) 80]. The said liquid (a), (b), (c) or (d) may optionally contain at least one humectant, for example glycerol, propylene glycol or a low molecular weight polyethylene glycol, for example a polyethylene glycol having a molecular weight in the range 190 to 600, for example polyethylene glycol 300.

In the case where the said coloured intagliated articles are film coated and the film coating agent is relatively insoluble in water, for example ethylcellulose, shellac or an acrylic resin, a suitable liquid is, for example:

(e) a polyhalogenated (1–4C)alkane, for example methylene dichloride;
(f) a dialkyl ketone of not more than 6 carbon atoms, for example acetone;
(g) a mixture of liquids (e) and (f); or
(h) a mixture of liquid (g) and a (1–4C)alkanol, for example methanol.

The said liquid (e), (f), (g) or (h) may optionally contain at least one plasticiser which is known in the art to be a suitable plasticiser for the relatively water-insoluble film coating agent in question, for example a di-(1–4-C)alkyl phthalate, for example diethyl phthalate or di-n-butyl phthalate, or an ester of glycerol with an alkanoic acid, for example glycerol triacetate or glyceryl monostearate, or a vegetable oil, for example castor oil.

The said suspension is applied in a conventional coating apparatus, for example a coating pan, or a coating drum, for example a side-vented perforated drum coating machine, or a so-called Wurster coating machine. However, it is important that the suspension is applied in the coating apparatus in such a way that a rubbing action takes place between the intagliated articles.

According to a further, preferred, feature of the invention there is provided a process for the manufacture of coloured solid articles bearing at least one highlighted intagliation, which comprises:

(a) applying the coloured intagliated articles, which themselves may be uncoated or film coated, a suspension comprising at least one optically anisotropic substance, having a minimum refractive index not greater than 2.00, in a suitable liquid in which the optically anisotropic substance is insoluble or of relatively poor solubility, which process is carried out in a conventional film coating apparatus in such a way that a rubbing action takes place between the articles being coated; and then (b) applying in conventional manner at least one film coating solution or suspension comprising at least one film coating agent, optionally at least one film coating adjuvant, and optionally at least one colouring agent.

Suitable film coating adjuvants and colouring agents are described above. The film coat(s) may be applied in step (b) using an organic solvent-based process, for example a process involving a mixture of methylene dichloride and methanol, or an aqueous process.

It is to be understood that, if desired, as a final step the highlighted products of the invention may be polished in conventional manner using at least one wax, for example beeswax or carnauba wax, so as to impart an attractive appearance to said products.

The invention is illustrated but not limited by the following Examples:

EXAMPLE 1

Approximately 100 differently coloured, film coated, intagliated tablets (a mixture of placebo tablets and medicinal tablets having a weight range of 95 to 650 mg.) were added to approximately 26,000 380mg. white tablets. The mixture of tablets was heated to 60° C. in a side-vented perforated coating drum (24 inch Accela-Cota machine; obtainable from Manesty Machines PLC, Speke, Liverpool 24, England). One liter of a 3% w/w aqueous suspension of light magnesium carbonate was applied continuously at 50 ml. min.$^{-1}$ by means of a low pressure air-spray unit. The drum speed was kept at 16 r.p.m. and the temperature of the inlet air at 60° C. When the suspension had all been applied the drum was stopped and the tablets removed. There were thus obtained inter alia coloured tablets with intagliations highlighted in white.

EXAMPLE 2

The process described in Example 1 was repeated and the tablets so produced were film coated in the 24 inch Accela-Cota machine with one liter of a 3.3% w/w aqueous solution of hydroxypropyl methylcellulose ['Pharmacoat' (Trade Mark) 606, Shin-Etsu Chemical Company Limited, Tokyo, Japan] containing 0.65% w/w of polyethylene glycol 300. The solution was applied under the conditions described in Example 1. When the solution had all been applied the drum was stopped and the tablets removed. There was thus obtained film coated coloured tablets with intagliations highlighted in white.

EXAMPLE 3

50,000 200 mg. white intagliated medicinal tablets were heated to 60° C. in a side-vented perforated drum coating machine (24 inch Accela-Cota). 2.6 liters of a 9% w/v aqueous solution of hydroxypropyl methylcellulose ['Pharmacoat' (Trade Mark) 606] containing 1.4% w/v glycerol and pink pigment dispersion [175 g.; 'Opaspray' (Trade Mark) pink, Colorcon PLC, Orpington, Kent, England] were applied continuously at 50 ml. min.$^{-1}$ by means of a low pressure air-spray unit. The drum speed was kept at 12 r.p.m. and the temperature of the inlet drying air at 60° C. When all of the suspension had been applied the drum was stopped and the tablets removed. There were thus obtained pink film coated intagliated tablets.

The said pink film coated intagliated tablets were heated at 60° C. in a side-vented perforated drum coating machine (24 inch Accela-Cota). 2 liters of a 1.5% w/v suspension of light magnesium carbonate in 1:1 v/v methanol/methylene dichloride were applied continuously at 300 ml. min.$^{-1}$ by means of a high pressure air-less spray unit. The drum speed was kept at 15 r.p.m. and the temperature of the inlet air at 60° C. When all of the suspension had been applied the drum was stopped and the tablets removed. There were thus obtained pink tablets having intagliations highlighted in white.

EXAMPLE 4

Approximately 100 film coated intagliated tablets (a mixture of medicinal tablets of three colours: carmine, brown and orange, having a weight range of 400–475 mg.) were added to approximately 52,000 190 mg. White placebo tablets. The mixture of tablets was heated to 60° C. in a side-vented perforated coating drum (24 inch Accela-Cota machine). One liter of a 4.5% w/w aqueous suspension of calcium carbonate was applied continuously at 50 ml. min.$^{-1}$ by means of a low pressure air-spray unit. The drum speed was kept at 16 r.p.m. and the temperature of the inlet air was kept at 60° C. When the suspension had all been applied the drum was stopped and the tablets removed. There were thus obtained carmine, brown and orange tablets, respectively, with the intagliations highlighted in white.

EXAMPLE 5

The process described in Example 4 was repeated except that aluminium hydroxide was used in place of calcium carbonate.

EXAMPLE 6

The process described in Example 4 was repeated, and the resulting mixed batch of tablets was heated to 60° C. in a side-vented perforated coating drum (24 inch Accela-Cota machine). 500 ml. of a 3% w/v aqueous solution of hydroxypropyl methylcellulose ('Pharmacoat' 606) containing 0.6% w/v glycerol as plasticiser and Brillant Blue F.C.F. water-soluble dye (Food, Drugs and Cosmetics Blue No. 1; 0.25 g.) was applied continuously at 50 ml. min.$^{-1}$ by means of a low pressure air-spray unit. The drum speed was kept at 16 r.p.m. and the temperature of the inlet air was kept at 60° C. When the solution had all been applied the drum was stopped and the tablets removed. There were thus obtained mauve tablets with the intagliations highlighted in blue (from the original carmine tablets), black tablets with the intagliations highlighted in blue (from the original brown tablets), and brown tablets with the intagliations highlighted in blue (from the original orange tablets).

What we claim is:

1. A solid article comprising a pharmaceutical or veterinary unit dosage form which is uniformly coloured over its entire surface and which bears at least one highlighted intagliation on its surface, said article bearing a coating layer over its entire surface including the intagliation and consisting essentially of at least one optically anisotropic substance having a minimum refractive index not greater than 2.00, the colour of the non-intagliated surface of said article being essentially unchanged by said layer while the colour of the intagliation is highlighted against the rest of the surface by said layer, said layer wherein said layer is applied by a coating process that consists essentially of applying a suspension said dosage containing said anisotropic substance on said dosage form in such a way that a rubbing action takes place between the dosage forms being coated containing no film coating agent.

2. An article as claimed in claim 1 containing a medicinal or veterinary agent, in which the said medicinal or veterinary agent is also used as the optically anisotropic substance.

3. An article as claimed in claim 1 which is a pharmaceutical or veterinary tablet.

4. An article as claimed in claim 1 in which, underneath the layer consisting essentially of at least one optically anisotropic substance, there is a film coat comprising at least one film coating agent and at least one colouring agent.

5. An article as claimed in claim 1 in which the optically anisotropic substance is white.

6. An article as claimed in claim 5 in which the optically anisotropic substance is magnesium carbonate, sucrose, lactose or tartaric acid.

7. An article as claimed in claim 5 in which the optically anisotonopic substance is a transparent white pigment.

8. An article as claimed in claim 1 which carries, on top of the layer consisting essentially of at least one optically anisotropic substance, at least one film coat comprising at least one film coating agent.

9. An article as claimed in claim 8 in which the film coat comprises at least one colouring agent.

* * * * *